(12) United States Patent
Patrick

(10) Patent No.: US 7,980,507 B2
(45) Date of Patent: Jul. 19, 2011

(54) INSERT FOR ROLL PAPER PRODUCTS

(76) Inventor: David O. Patrick, Cape Girardeau, MO (US)

( * ) Notice: Subject to any disclaimer, the term of this patent is extended or adjusted under 35 U.S.C. 154(b) by 0 days.

(21) Appl. No.: 12/857,509

(22) Filed: Aug. 16, 2010

(65) Prior Publication Data

US 2011/0133014 A1 Jun. 9, 2011

Related U.S. Application Data

(63) Continuation-in-part of application No. 12/591,942, filed on Dec. 4, 2009.

(51) Int. Cl.
*B65H 16/06* (2006.01)

(52) U.S. Cl. .................. 242/596.7; 242/598.3; 242/599; 242/905

(58) Field of Classification Search .................. 242/599, 242/596.7, 905, 598, 598.2–598.4
See application file for complete search history.

(56) References Cited

U.S. PATENT DOCUMENTS

| | | | |
|---|---|---|---|
| 2,293,785 A | 8/1942 | Wintz | |
| 2,753,209 A | 7/1956 | Klasky | |
| 2,806,738 A * | 9/1957 | Tsakalas | 239/52 |
| 2,873,928 A * | 2/1959 | Klasky | 242/599.3 |
| 2,901,790 A * | 9/1959 | Nielsen | 422/123 |
| 3,017,117 A * | 1/1962 | Klingler | 239/52 |
| 4,598,006 A * | 7/1986 | Sand | 514/291 |
| 4,759,510 A | 7/1988 | Singer | |
| 5,273,227 A | 12/1993 | Smith | |
| 5,381,984 A * | 1/1995 | Hindsgual | 242/613.5 |
| 5,494,218 A | 2/1996 | Armand | |
| 5,727,751 A | 3/1998 | Liu | |
| 6,425,530 B1 | 7/2002 | Coakley | |
| 6,575,383 B2 | 6/2003 | Dobler et al. | |
| 6,688,551 B1 * | 2/2004 | He et al. | 242/599 |
| 6,772,975 B2 * | 8/2004 | Sommerfeld et al. | 242/563.2 |
| 6,883,787 B2 * | 4/2005 | Allen | 261/30 |
| 6,969,024 B2 * | 11/2005 | He et al. | 242/599 |
| 2005/0098465 A1 | 5/2005 | Wolf | |
| 2009/0179105 A1 | 7/2009 | Owen et al. | |

* cited by examiner

*Primary Examiner* — Sang Kim
(74) *Attorney, Agent, or Firm* — Richard C. Litman

(57) ABSTRACT

The insert for roll paper products is pliable, preferably scent-impregnated, foam material that can be wrapped around a dispensing bar of a rolled paper dispenser, and resiliently grips the bar while adding friction to the total dispensing system. The dispensing bar and insert combination is then slid through the hollow core of a rolled paper product. The sleeve has dentate ends that extend beyond the ends of the paper roll. When the product core is rotated while paper is being dispensed, the passage of air through the dentate ends helps to dispense and distribute the scent through the environment proximate the paper dispenser. Moreover, the resilient foam insert provides friction between the paper roll and the foam structure, while also adding friction between the foam structure and the dispensing bar. This feature acts as a brake to prevent excess rollout of the rolled product when being dispensed.

1 Claim, 11 Drawing Sheets

INSERT FOR ROLL PAPER PRODUCTS

CROSS-REFERENCE TO RELATED APPLICATION

This application is a continuation-in-part of U.S. patent application, Ser. No. 12/591,942 filed Dec. 4, 2009.

BACKGROUND OF THE INVENTION

1. Field of the Invention

The present invention relates generally to devices for dispensing paper on a roll, and particularly to an insert for roll paper products that provides a scent during rollout and use of the rolled paper.

2. Description of the Related Art

Every modern bathroom is equipped with a toilet paper dispenser for dispensing disposable toilet tissue from a roll for hygienic purposes. Nevertheless, using the bathroom may still prove unpleasant because of the odors associated with the toilet. Many bathrooms are equipped with an exhaust fan to help alleviate this problem. However, such exhaust fans provide only a partial solution to the problem. Stand-alone air fresheners are of some help. But stand-alone air fresheners often go stale, aren't replaced regularly, lack sufficient strength for overcoming toilet odors, and are frequently knocked over, even if there's a place to put them in the bathroom. There is a need for a better solution to the problem of toilet odor in the bathroom. Additionally, there is a need to prevent excessive rollout of toilet paper and other types of rolled paper products when being dispensed.

Thus, an insert for roll paper products solving the aforementioned problems is desired.

SUMMARY OF THE INVENTION

The insert for roll paper products is a pliable, preferably scent-impregnated, foam sheet that is coil wrapped over the dispensing bar of a rolled paper dispenser, so that it can resiliently grip the bar by adding friction to the total dispensing system. The dispensing bar and insert combination is then slid through the hollow core of a rolled paper product, e.g., toilet paper, paper towels, etc. The sleeve has dentate ends that extend beyond the ends of the paper roll. When the product core is rotated while paper is being dispensed, the passage of air through the dentate ends helps to dispense and distribute the scent through the environment proximate the paper dispenser. Moreover, the coiled structure of the wrapped resilient foam provides friction between the paper roll and the foam structure, while also adding friction between the foam structure and the dispensing bar. This feature acts as a brake to prevent excess rollout of the rolled product when being dispensed.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
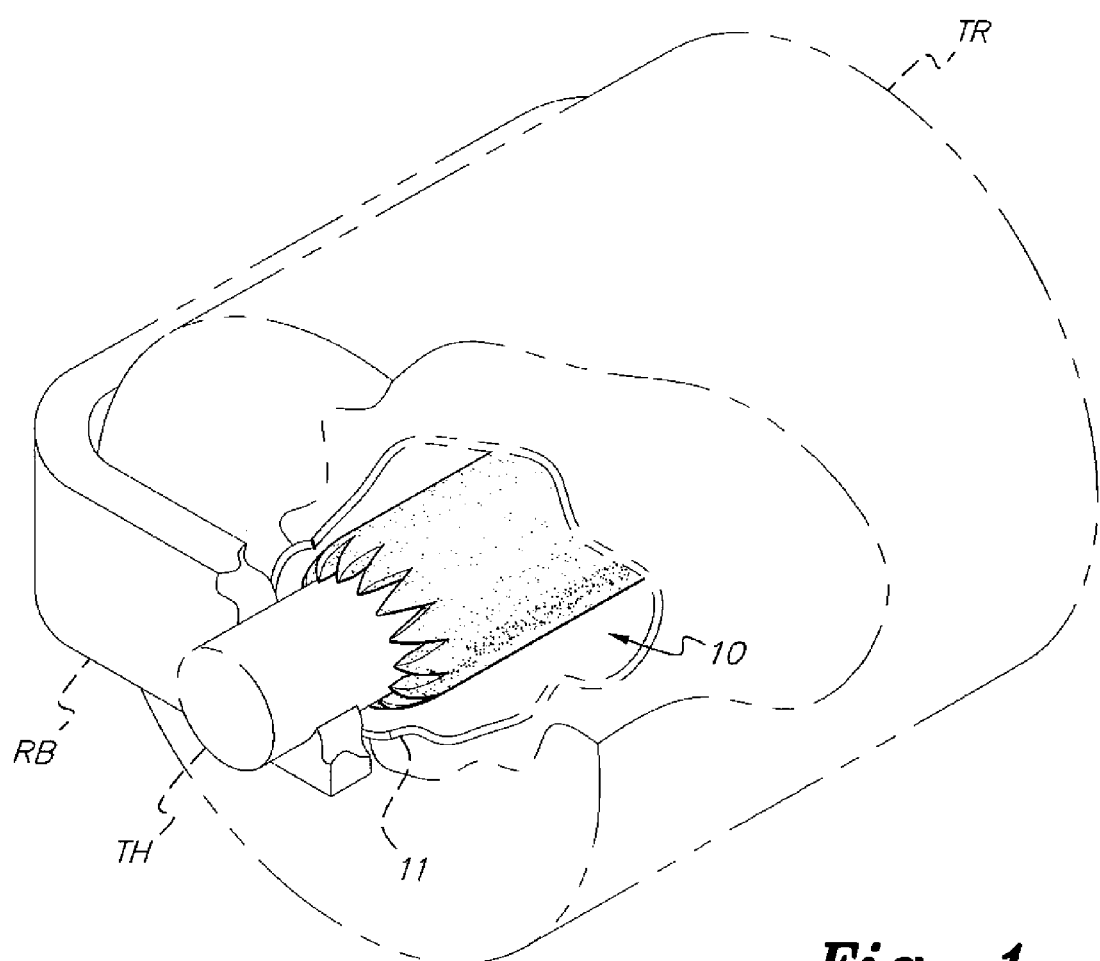
FIG. 1 is an environmental, perspective view of an insert for roll paper products according to the present invention.
Figure 2:
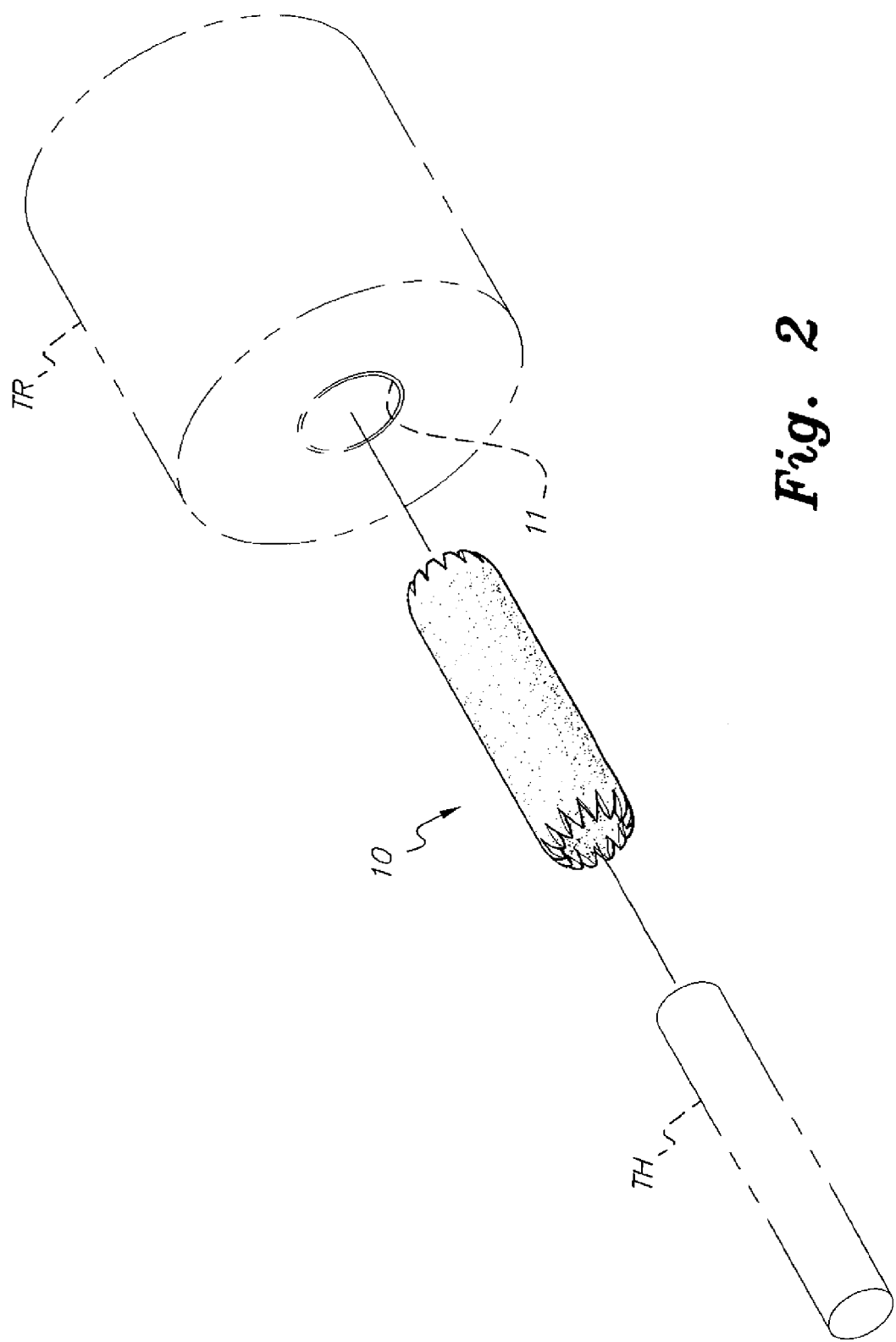
FIG. 2 is a perspective view of the scented foam insert according to the present invention.
Figure 3:
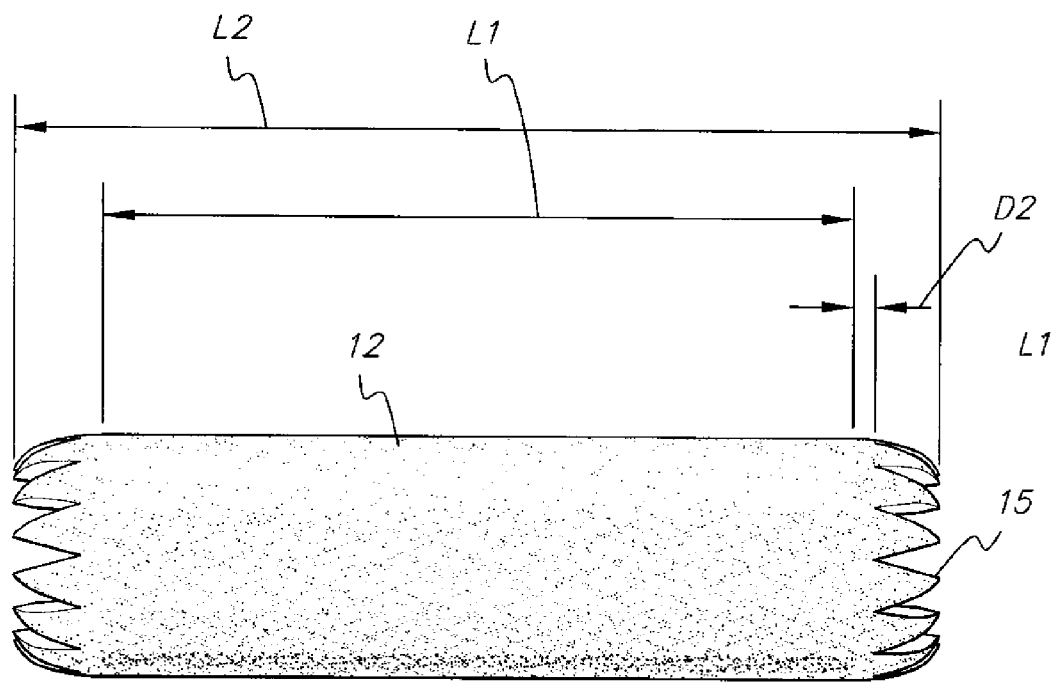
FIG. 3 is a front view of the scented foam insert according to the present invention.

As shown in FIGS. 1-3, the insert for roll paper products, designated generally as 10 in the drawings, is a pliable, scent-impregnated foam sheet which can be rolled into a hollow substantially cylindrical sleeve that wraps around a dispenser bar TH of a toilet paper dispenser RB. The sleeve is preferably sufficiently resilient that it grips the roller, i.e., dispenser bar TH. The insert sleeve 10 and dispenser bar TH combination can then be inserted through the hollow core 11 of a roll TR of toilet paper and mounted on the dispenser RB. The wrapped cylindrical insert 10 has dentate ends that define teeth or vanes 15.

Figure 4:
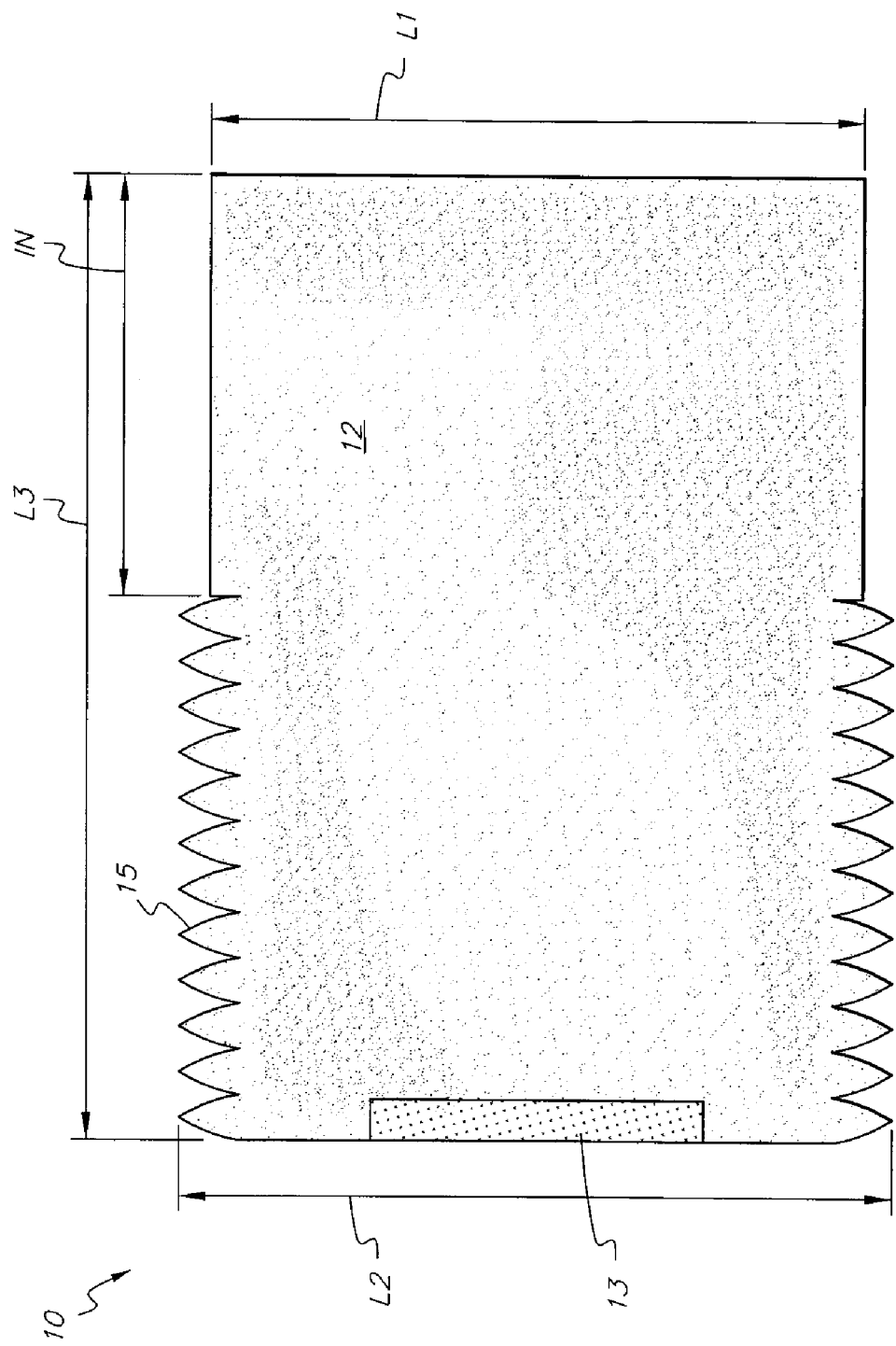
FIG. 4 is a plan view of the scented foam insert according to the present invention, shown unrolled.

As shown in FIG. 4 the exemplary insert 10 is a substantially rectangular sheet made from a resilient foam material, the sheet having longitudinally extending parallel opposing edges having length dimension L3 which exceeds dimension L1 of first lateral end or exceeds dimension L2 of second lateral end. A portion of the longitudinally extending parallel opposing edges includes dentate structures defining vanes 15. An adhesive strip 13 is disposed on an inner portion of rectangular sheet 10 proximate the second end of insert 10.

Figure 5:
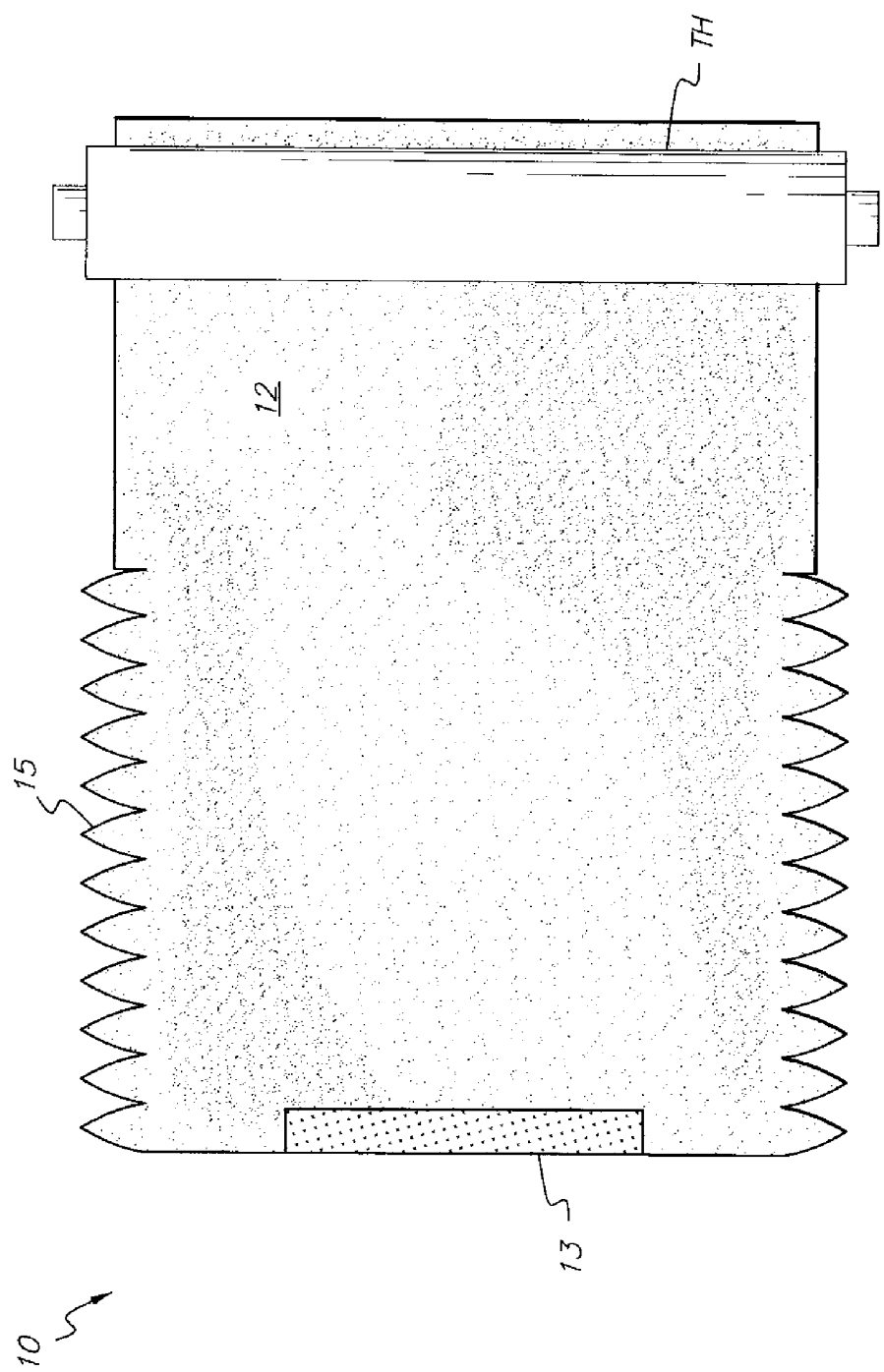
FIG. 5 is a top plan view of the insert of FIG. 4, showing the dispenser bar on the insert.
Figure 6:
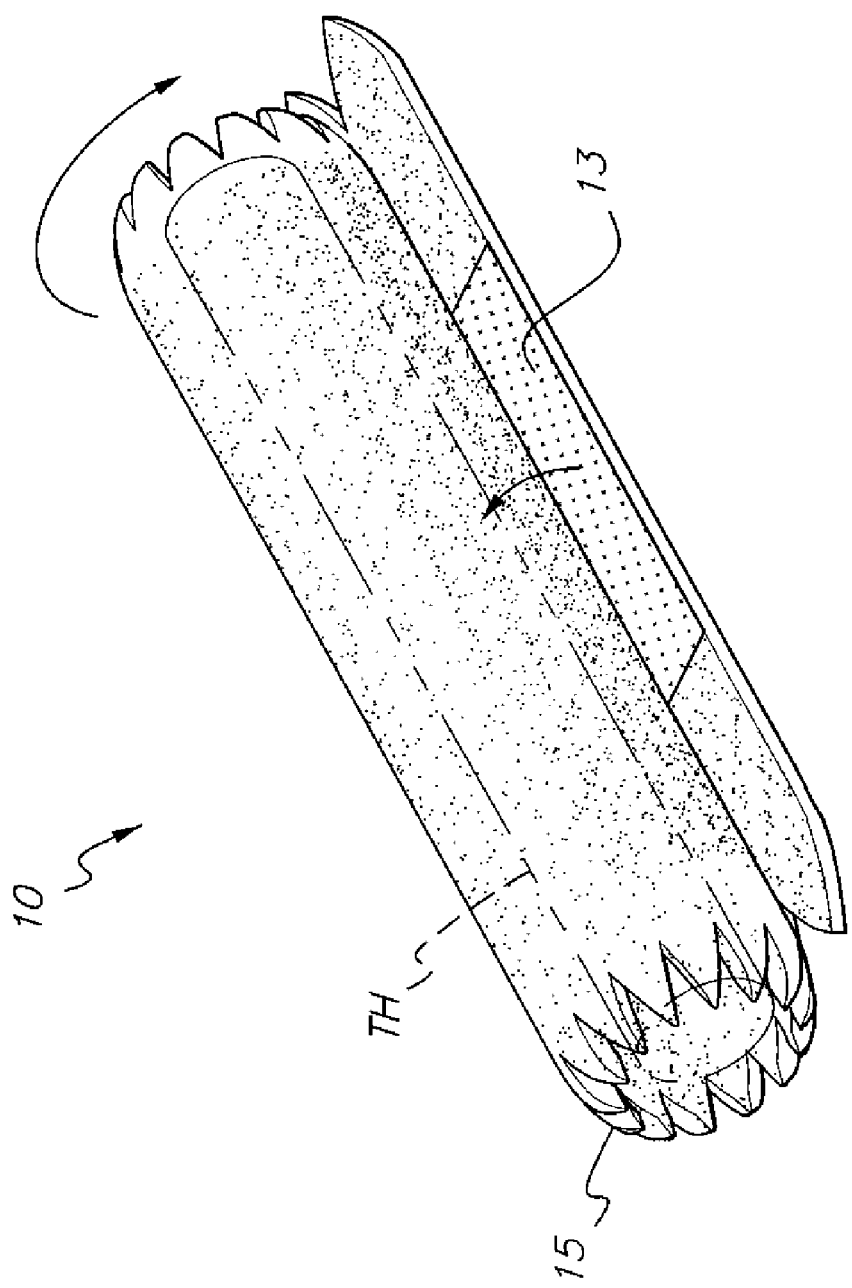
FIG. 6 is a perspective view of the insert of FIG. 4, showing the insert partially rolled onto the dispenser bar.

As shown in FIG. 5, the first end of the rectangular sheet 10 can be placed in contact with a paper roll dispensing bar TH such that the paper roll dispensing bar is parallel to the first end. As shown in FIG. 6, the insert sheet 10 is then wrapped, i.e., coiled around the paper roll dispensing bar TH. This configuration of the insert 10 and dispensing bar TH results in frictional contact between the insert 10 and the paper roll dispensing bar TH.

Figure 8:
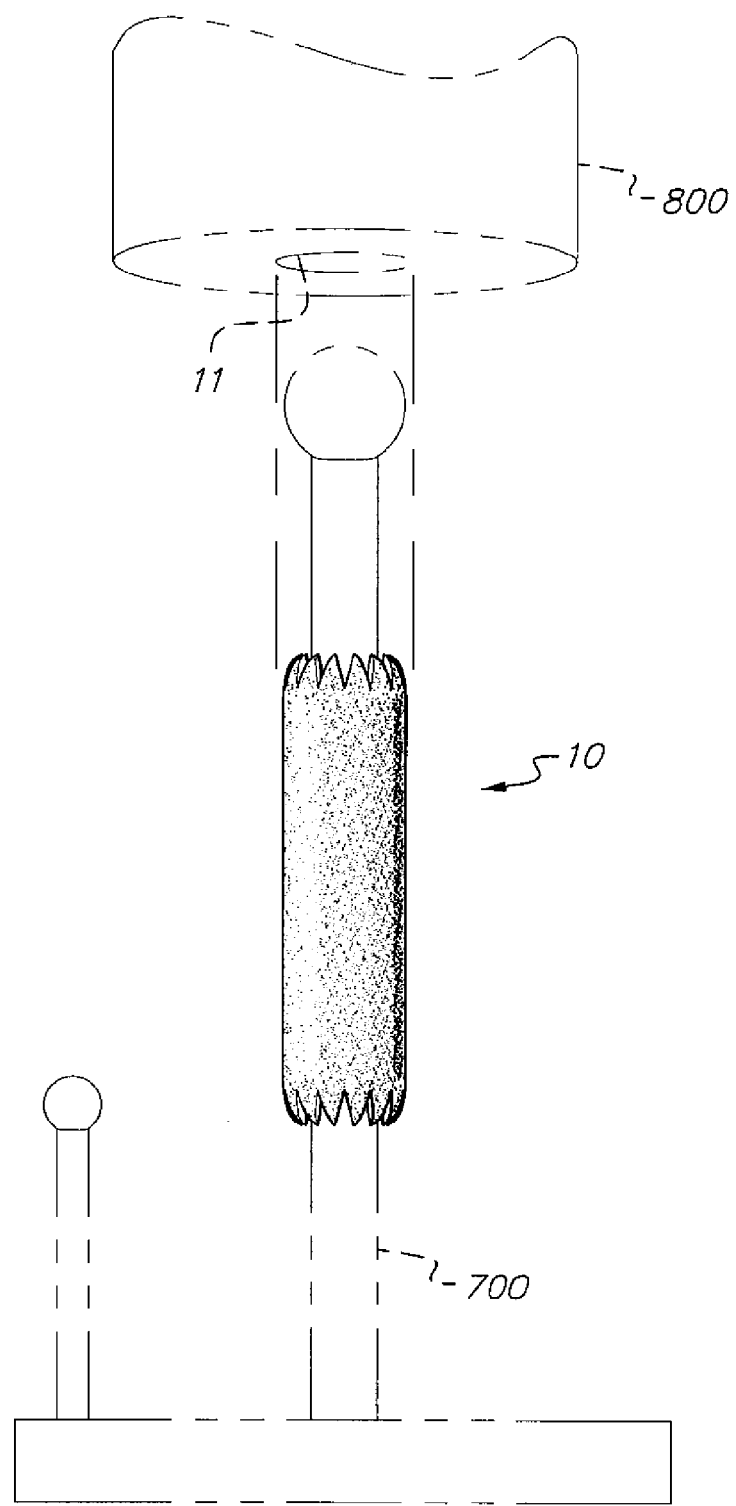
FIG. 8 is a partially exploded environmental front view of the insert of FIG. 7, showing the paper towel roll being prepared for insertion over the insert.

The adhesive strip 13 is designed to contact an outer portion of the coiled sheet insert 10 to retain the coiled sheet insert 10 in contact with the roll dispensing bar TH. As shown in FIGS. 1, 2, and 8, the coiled sheet 10 is inserted into a hollow cylindrical core 11 of a roll paper product, outer resilient portion of coiled sheet insert 10 also being in frictional contact with the hollow cylindrical core 11 of the roll paper product.

When the dispensing bar TH is affixed to dispensing bar retaining hardware the paper product such as toilet paper roll TR or paper towel roll 800 can be unrolled in controlled portions without excessive rollout due to braking effect of the frictional contact of the inserted coiled sheet insert 10.

Figure 7:
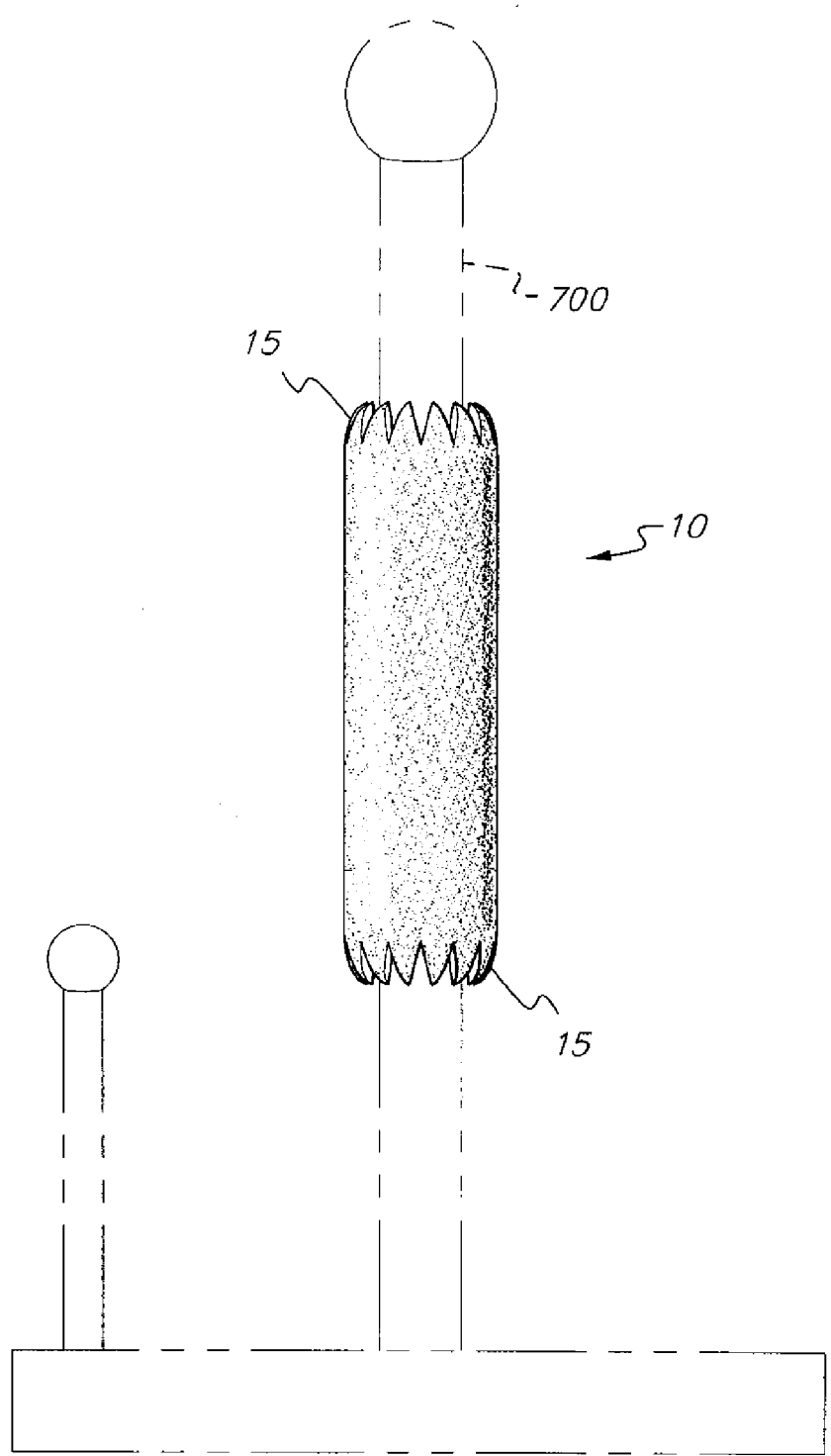
FIG. 7 is an environmental front view of an insert according to the present invention, shown mounted on a freestanding paper towel dispenser bar.
Figure 9:
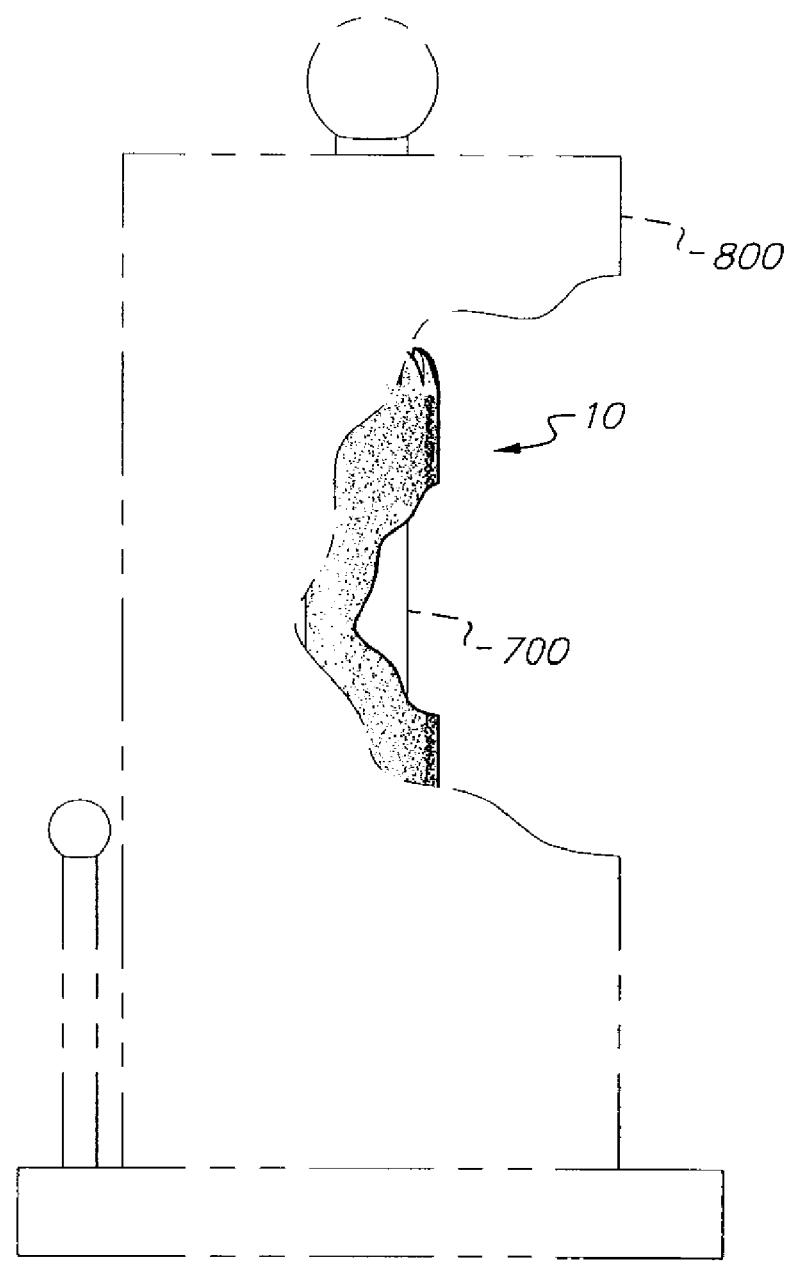
FIG. 9 is an environmental front view of the paper towel dispenser of FIGS. 7-8, shown with both the paper towel roll and the insert broken away to show details thereof.

The insert 10 can be used with a wide variety of rolled paper products and their dispensers. For example, as shown in FIG. 7, the insert can be wrapped and secured around a free-standing paper towel dispenser bar 700, and, as shown in FIGS. 8-9, configured for frictional contact with the core of towel paper roll 800 and free-standing dispenser bar 700.

Figure 10:
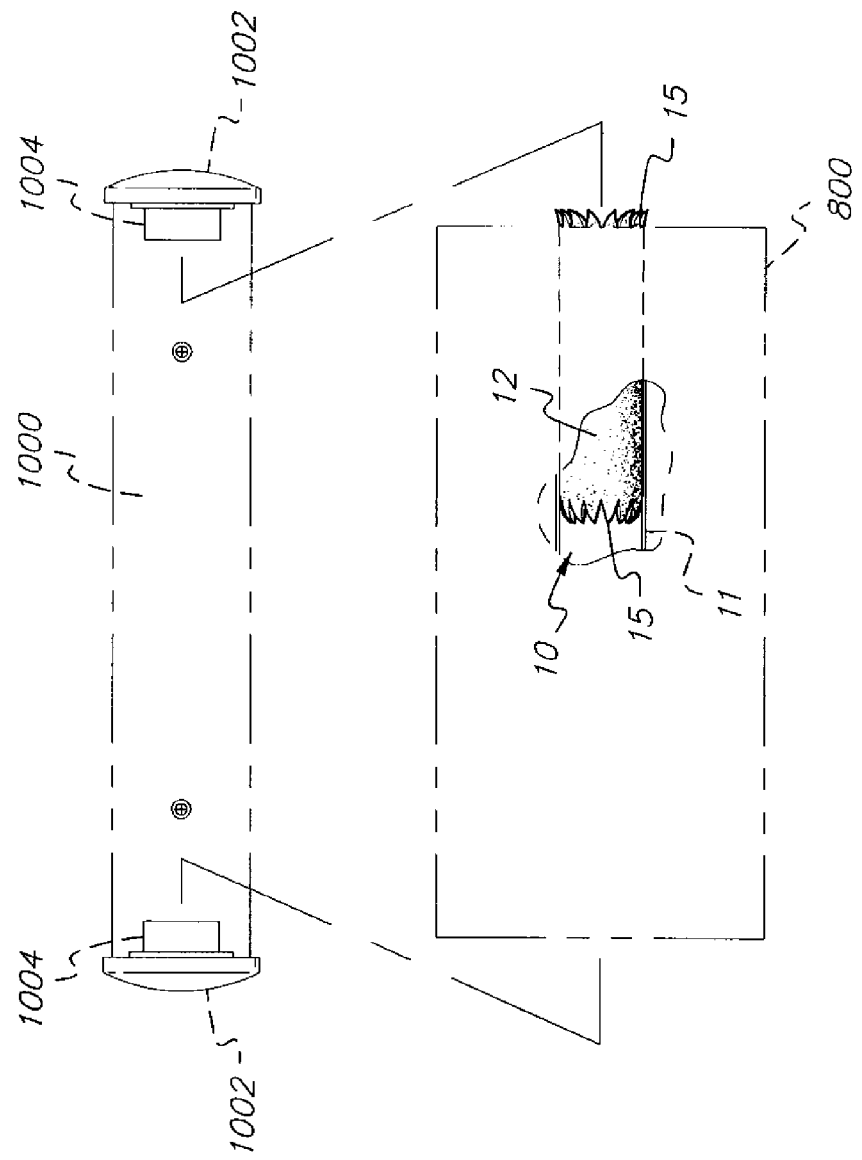
FIG. 10 is an environmental front view of an alternative paper towel dispenser, shown with the insert and the roll of paper towels exploded from the dispenser bracket.
Figure 11:
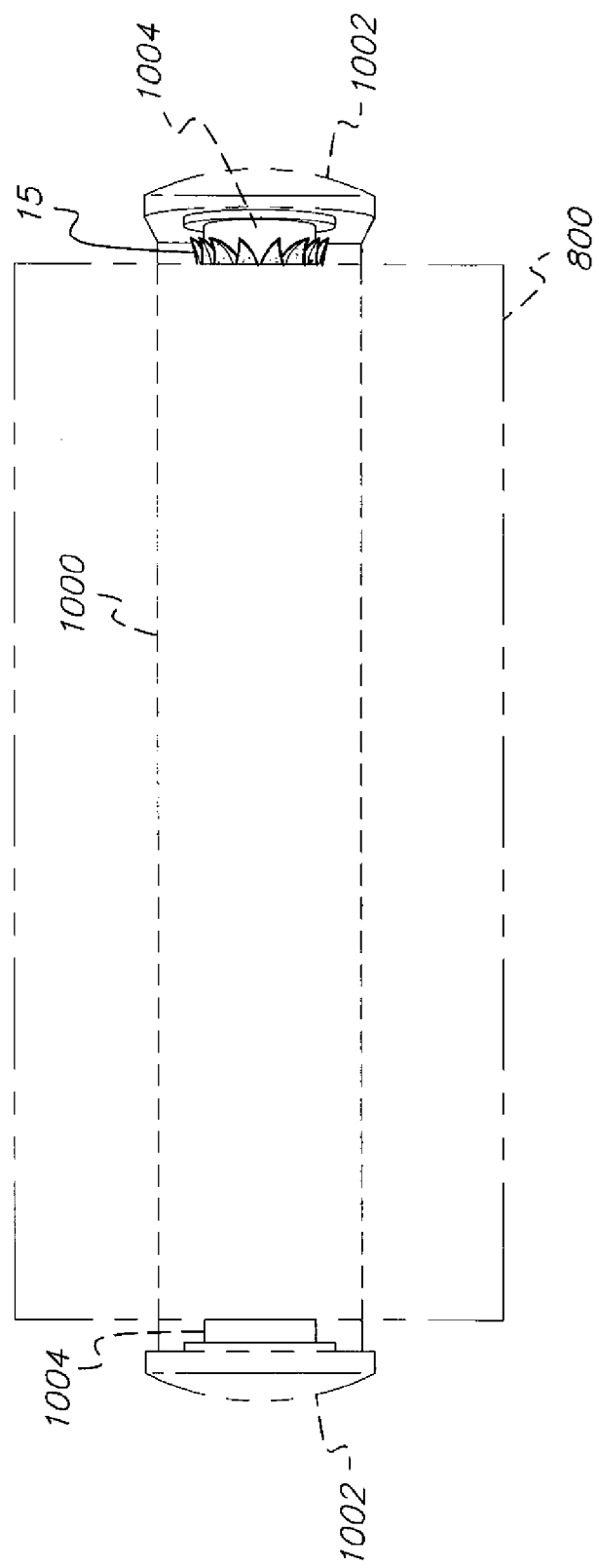
FIG. 11 is an environmental front view of the paper towel dispenser of FIG. 10, showing the roll insert and paper towel attached to the dispensing unit.

As shown in FIGS. 10-11 the insert 10 can also be used with a wall mounted paper towel dispenser. Such a dispenser has a wall mounted bracket 1000 which extends to support laterally separated cylindrical paper roll retainers 1004, each cylindrical roll retainer 1004 having an end cap 1002. Notwithstanding the fact that the dispenser shown in FIGS. 10-11 has no dispenser bar, the inventive insert 10 can be configured inside paper roll 800 such that dentate vanes 15 extend out of one end of the paper roll 800. There is frictional contact between body of insert 10 and core 11 of paper roll 800. Ends of the paper roll 800 are then attached to the dispenser's roll retainers 1004, the dentate vanes 15 coming in frictional contact with at least one of the roll retainers 1004. This configuration allows the insert 10 to still function as a brake when paper is dispensed from roll 800 using the dispenser shown in FIGS. 10 and 11.

As most clearly shown in FIGS. 1 and 3, the dimensions of L1, L2, and D2 are formulated so that the vanes 15 extend beyond the ends of a toilet paper roll TR, preferably by about ⅜" on each side. During rollout of the paper, the rotating vanes 15 facilitate dispersal of the scent, the teeth or vanes 15 maximizing the surface area exposed to the air during rotation of the roller. The foam sleeve 10 emanates a pleasant fragrance during rollout and use of the paper in order to mask or neutralize toilet odors.

As shown in FIG. 4, the preformed shape 12 of insert 10 is substantially planar and rectangular having a total length L3 and a total width L2. Preferable total length L3 is approximately 8 inches. Preferable total width L2 is approximately 5.9062 inches. Preferable width L1 of portion IN is approximately 5.4063 inches. Portion IN preferably extends 3.5000 inches beyond dentate portion 15. When the device 10 is formed into a roll, extended portion IN is tucked inside the roll and glued or otherwise fastened to remainder of inside roll portion to stably affix the roll into a cylindrical form.

The insert 10 may be made from any suitable foam material, such as foam rubber, polyurethane, polystyrene, or other resilient foam material. The scent may be any suitable fragrance, natural or synthetic.

It is to be understood that the present invention is not limited to the embodiments described above, but encompasses any and all embodiments within the scope of the following claims.

I claim:

1. An insert for roll paper products, comprising:
a substantially rectangular sheet made from a fragrance impregnated resilient foam material, the sheet consisting of longitudinally extending parallel opposing edges, a portion of said longitudinally extending parallel opposing edges including dentate structures defining vanes, wherein the vanes constitute the opposing edges and aide in dispersal of the fragrance from the sheet into ambient air when the paper product is being dispensed from the paper product roll, the sheet having a first end and a second end defining lateral edges of the sheet, the first end being rolled towards the second end to form a substantially cylindrical shape;
an adhesive strip disposed on an inner portion of the rectangular sheet proximate the second end, the adhesive strip contacting an outer portion of the cylindrically shaped sheet, thereby retaining the shape for insertion into a hollow cylindrical core of a roll paper product;
wherein the sheet is adapted for being wrapped around a dispenser bar and secured thereto by the adhesive strip, the sheet being adapted for frictionally engaging a core of a rolled paper product so that the paper product can be unrolled in controlled portions due to braking effect of friction between the insert and the rolled paper product core.

* * * * *